United States Patent [19]

Huibers et al.

[11] 4,420,644

[45] Dec. 13, 1983

[54] LIGNIN HYDROCRACKING PROCESS TO PRODUCE PHENOL AND BENZENE

[75] Inventors: Derk T. A. Huibers, Pennington; Hugh J. Parkhurst, Jr., Plainsboro, both of N.J.

[73] Assignee: Hydrocarbon Research, Inc., Lawrenceville, N.J.

[21] Appl. No.: 295,459

[22] Filed: Aug. 24, 1981

[51] Int. Cl.$^3$ .............................................. C07C 37/00
[52] U.S. Cl. ..................................... 568/806; 568/799
[58] Field of Search ....................... 568/806, 805, 799

[56] References Cited

U.S. PATENT DOCUMENTS

| | | | |
|---|---|---|---|
| 2,328,749 | 9/1943 | Sherrard et al. | 568/806 |
| 2,746,996 | 5/1956 | Neuworth | 568/806 |
| 2,786,873 | 3/1957 | Ohsol et al. | 568/805 |
| 2,947,739 | 8/1960 | Gaslini | 568/806 |
| 2,991,314 | 7/1961 | Giesen | 568/806 |
| 2,998,457 | 8/1961 | Paulsen | 568/806 |
| 4,258,221 | 3/1981 | Knudsen et al. | 568/806 |

*Primary Examiner*—Werren B. Lone
*Attorney, Agent, or Firm*—V. A. Mallare; F. A. Wilson

[57] ABSTRACT

A lignin-containing feed material in particulate form is mixed with a process-derived slurrying oil and fed into an ebullated catalyst bed hydrocracking reactor. Reaction conditions are maintained at 650°–850° F. temperature, 500–2500 psig hydrogen partial pressure and space velocity of 1.0–10 wt. lignin/hr./wt. catalyst. The reaction products are phase separated to recover hydrogen and slurrying oil, and the resulting liquid stream is passed to a thermal hydrodealkylation step. The reacted stream is fractionated to produce phenol and benzene products, along with a heavy alkylated material which is recycled to the hydrodealkylation step to increase the yield of phenol and benzene.

9 Claims, 3 Drawing Figures

ESTIMATED BOND ENERGIES OF GUAIACYL MOIETIES
(KCAL/MOLE)

ESTIMATE OF THE PERCENTAGE BOND
CLEAVAGE IN CATALYTIC HYDROCRACKING
OF A KRAFT LIGNIN MOIETY, TO PRODUCE
MIXED PHENOLS.

LIGNIN HYDROCRACKING PROCESS TO PRODUCE PHENOL AND BENZENE

This invention pertains to the catalytic hydrocracking of lignin-containing feedstocks to produce mono-aromatic phenol-containing products. It pertains particularly to such lignin hydrocracking process followed by hydrodealkylation of the mono-aromatic liquid to produce phenol and benzene products.

BACKGROUND OF INVENTION

Lignin is an aromatic polymer found in all vascular plants. It is currently produced as a co-product of paper pulp and burned for its fuel value. When petroleum feedstock was cheap, lignin was not worth recovering as a chemical feedstock. However, as petroleum feedstocks become scarcer and more expensive, and an ever increasing percentage comes from foreign sources, more consideration is being given to using lignin, which is a domestic renewable feedstock, as a source of mono-aromatics products, particularly phenol.

Lignin comprises roughly 25% of lignocellulosic biomass, which includes all vascular plants. Lignin gives plants rigidity and protection and helps regulate the permeation of water. It is formed within the plant primarily by the dehydrogenative polymerization of three precursors: trans-coniferyl, trans-sinapyl and trans-p-coumaryl alcohol. The relative amounts of each component and their linkages vary with wood types. Trans-coniferyl alcohol is always the major component, and hardwood lignins contain more trans-sinapyl structures.

In wood pulping via the kraft process, cellulose, hemicellulose and lignin are separated by dissolving hemicellulose and lignin in an alkaline sodium sulfate/sulfide solution at elevated temperature and pressure, yielding the so-called black liquor. Wood lignin is considerably changed by kraft cooking. Condensations involving formaldehyde or active beta-carbonyl derivatives leads to methylene linked aromatic rings and an increase in molecular weight. At the same time, alkaline cleavage of phenolic ethers occurs. As a result of the alkaline cleavage, phenolic hydroxyls increase from 0.3 per monomer in the protolignin to almost 1.0 in the dissolved lignin.

When sufficiently depolymerized, the lignin phenolate form dissolves in the black liquor. The phenolic groups can be liberated by acidification with carbon dioxide obtained from stack gases. This causes the lignin to precipitate, aided by the salting-out effect of the sodium salts of the black liquor. Lignin is filtered at 60°–80° C. Further purification by solution in dilute alkali and reprecipitation with sulfuric acid gives a kraft lignin, such as that used as feedstock in our invention (Table 1). Kraft lignin has a typical average molecular weight of about 3500, which indicates that the average softwood kraft lignin is comprised of about 20 starting units.

TABLE 1
ANALYSIS OF KRAFT LIGNIN CHARGE STOCK (W %)

| | | |
|---|---|---|
| Ash by Combustion | | 1.40 |
| Water | | 1.02 |
| Carbon | (organic) | 64.89 |
| Carbon | ($Na_2CO_3$) | 0.08 |
| Hydrogen | (ex. $H_2O$) | 5.67 |
| Sulfur | ($Na_2SO_4$) | 0.16 |
| Sulfur | (organic) | 1.19 |
| Oxygen | ($Na_2CO_3$ + $Na_2SO_4$) | 0.64 |
| Oxygen | (organic sulfur) | 0.60 |
| Oxygen | (organic) | 25.23 |
| Sodium | ($Na_2CO_3$ + $Na_2SO_4$) | 0.52 |
| | | 100.00 |
| Organic, W % | | |
| Carbon | | 64.89 |
| Hydrogen | | 5.67 |
| Oxygen | | 25.23 |
| | | 95.79 |

U.S. Pat. No. 2,328,749 to Sherrard discloses an early batch-type process for catalytic hydrogenation of wood material to remove lignin and make cellulose. Also, U.S. Pat. No. 2,947,739 to Gaslini discloses a process for hydrogenation of ligno-cellulosic materials using soluble metal carbonyl catalyst at relatively low temperature and pressure conditions. U.S. Pat. No. 2,991,314 to Giesen discloses a continuous non-catalytic process for cleavage of lignin to produce phenols at temperatures above 300° C. and pressure above 350 atm. to yield distillable lignin products. Also, hydrogenation of lignin using the Noguchi batch-type process developed in Japan is disclosed by Goheen in Adv. in Chem. Ser. No. 59,226 (1966). However, further process improvements are needed to develop a continuous process for hydrocracking lignin-containing feedstocks and produce high yields of useful phenol and benzene products along with some distillable oils.

SUMMARY OF INVENTION

This invention discloses a catalytic hydrocracking process for converting lignin-containing feedstocks to mono-aromatic phenol-containing products. The lignin-containing feed is first slurried with a process-derived oil and depolymerized by a hydrocracking reaction step. The resulting stream is then treated to recover a hydrogen-containing gas and aromatic fuel oil, a portion of which is recycled as slurrying oil. The remaining mono-aromatics are usually then hydrodealkylated to produce phenol and benzene products. The invention also discloses the chemistry of lignin hydrocracking and hydrodealkylation of the resulting intermediate materials to produce aromatic fuel oil and high yields of phenol and benzene products. A heavy alkylated material stream is recycled to the hydrodealkylation step for further reaction to increase the yield of phenol and benzene products.

The catalytic hydrocracking step, which is regarded as the best method for lignin depolymerization, is operated at sufficient temperatures so that the initiating step is thermal bond rupture to form free radical lignin fragments. This is followed by stabilization of these free radicals with hydrogen dissolved in the reaction slurry feedstream. In a parallel simultaneous reaction, a methyl radical is removed from the methoxy side group. In order to obtain good phenol yields, repolymerization to produce heavy oil and hydrogenation of the aromatic ring and more than one of the hydroxyl groups must be avoided.

FIG. 1 shows the estimated bond energies of the quaiacyl moieties as they occur in kraft lignin molecules. These bond energies are approximate and do not take into account interactions with other substituents. As discussed above, in lignin these quaiacyl moieties are linked, mostly with alkylaryl ether linkages; i.e., between a phenolic hydroxy group and the carbon atom of a side chain. In kraft lignin, part of these alkyl-aryl linkages are hydrolyzed, while new methylene linkages are formed. FIG. 1 shows the most likely places of thermal bond rupture, which are:

(a) alkyl-aryl linkages between quaiacyl-type moieties;
(b) methyl-oxygen linkages of the methoxy groups attached to the aromatic ring; and
(c) methylene linkages between quaiacyl moieties.

Only after thermal bond rupture, which reduces lignin to at most a quaiacyl-type tetramer, can the hydrocracking catalyst play a useful role, as whole kraft lignin molecules are too large to enter the catalyst pores. Upon entering the catalyst, further depolymerization of the lignin tetramer and removal of substituents will occur.

In our process, the hydrocracking reaction conditions are maintained within the broad range of 650°–850° F. temperature and 500–2500 psig hydrogen partial pressure. The feed rate or space velocity is maintained within the range of 1.0–10 pound lignin/hr.-/pound catalyst and preferably 0.3–6 pound lignin/hr.-/pound catalyst (WHSV). The lignin-containing feed will have particle size smaller than about 40 mesh (0.016 inch). Useful particulate catalysts comprise oxides of iron, cobalt, molybdenum or nickel, or combination thereof, on a support comprising alumina, silica, or combination thereof. Catalyst particle size should be within the range of 0.020–0.130 inch effective diameter, and preferably 0.040–0.080 inch diameter.

A product yield summary resulting from hydrocracking lignin in an ebullated bed catalytic reaction step is shown in Table 2. It shows that 37.5 W % of the "organic lignin" was converted to phenols. The 465°–500° F. fraction contains some catechol (b.pt. 474° F.). Table 3 shows a detailed analysis of the phenols fraction, leading to FIG. 2, which presents an estimate of the percentage of bond cleavage in catalytic hydrocracking of kraft lignin moieties to produce the observed mixture of phenols. FIG. 2 shows that the hydroxy groups in the 3-position are removed about five times as fast as the hydroxy groups in the 4-position. Of the total number of potentially available hydroxy groups, including those occurring in the proto-lignin as methyl ether, only 28% are retained.

Since only one hydroxy group per aromatic ring is desired, the selectivity of producing alkyl phenols in this particular experimental run was 56%. Of the remaining 44%, 11% can probably be found in fractions boiling above 465° F., which contain two hydroxy groups, while 33% of the aromatic rings lost both hydroxy groups. As shown in Table 2, 14.0 W % of the organic lignin was converted to aromatic hydrocarbons boiling below 465° F.

TABLE 2

| PRODUCT YIELD SUMMARY (Run 144-57-4) | |
|---|---|
| | W % of Organic Lignin |
| CO | 3.9 |
| $CO_2$ | 1.8 |
| $CH_4$ | 6.6 |
| $C_2H_6$ | 1.9 |
| $C_3H_8$ | 7.3 |
| $C_4H_8$ | 1.0 |
| $C_4H_{10}$ | 1.0 |
| $C_5H_{10}$ | 0.7 |

TABLE 2-continued

| PRODUCT YIELD SUMMARY (Run 144-57-4) | |
|---|---|
| | W % of Organic Lignin |
| $C_5H_{12}$ | 1.0 |
| Subtotal | 25.2 |
| $H_2O$ | 17.9 |
| $C_6$-300° F. Neutrals | 8.3 |
| 300°–465° F. Neutrals | 5.7 |
| 300° F.–465° F. Phenols | 37.5 |
| 465° F.–500° F. | 8.7 |
| 500° F.+ | 2.4 |
| Subtotal | 80.5 |
| Total | 105.7 |
| Chemical $H_2$ Consumption W % | 5.73 |

TABLE 3

| 300° F.–465° F. PHENOLS COMPOSITION (Analysis in W %) | |
|---|---|
| Run Number | 144-57-4 |
| Phenol | 6.54 |
| o-Cresol | 3.62 |
| m-Cresol | 11.88 |
| p-Cresol | 9.72 |
| 2,4 Xylenol | 7.01 |
| p-Ethylphenol | 33.22 |
| o-n-Propylphenol | 7.94 |
| p-n-Propylphenol | 20.07 |
| | 100.00 |

Hydrodealkylation of the mixed phenols can better be done in a separate reactor without a catalyst. Studies indicate that the molar selectivity for the thermal hydrodealkylation of cresols to phenols is about 60 mole %. About 37 mole % of the cresols is dehydroxylated and the remainder cracked to gas. To obtain this high selectivity, the reaction is run at a lower temperature and longer residence time than for conventional toluene hydrodealkylation. Conversion per pass is about 30%.

DESCRIPTION OF PREFERRED EMBODIMENT

Figure 1:
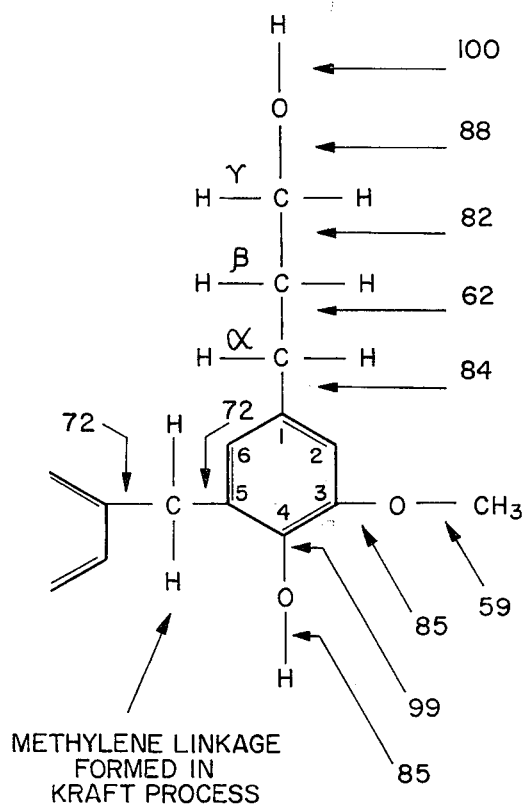
FIG. 1 is a diagram showing estimated bond energies for kraft process lignin molecules.
Figure 2:
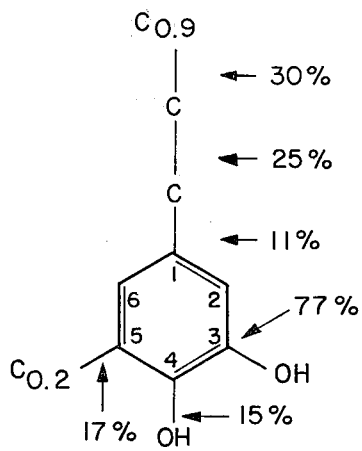
FIG. 2 is a diagram showing percentage bond cleavage in hydrocracking kraft lignin.
Figure 3:
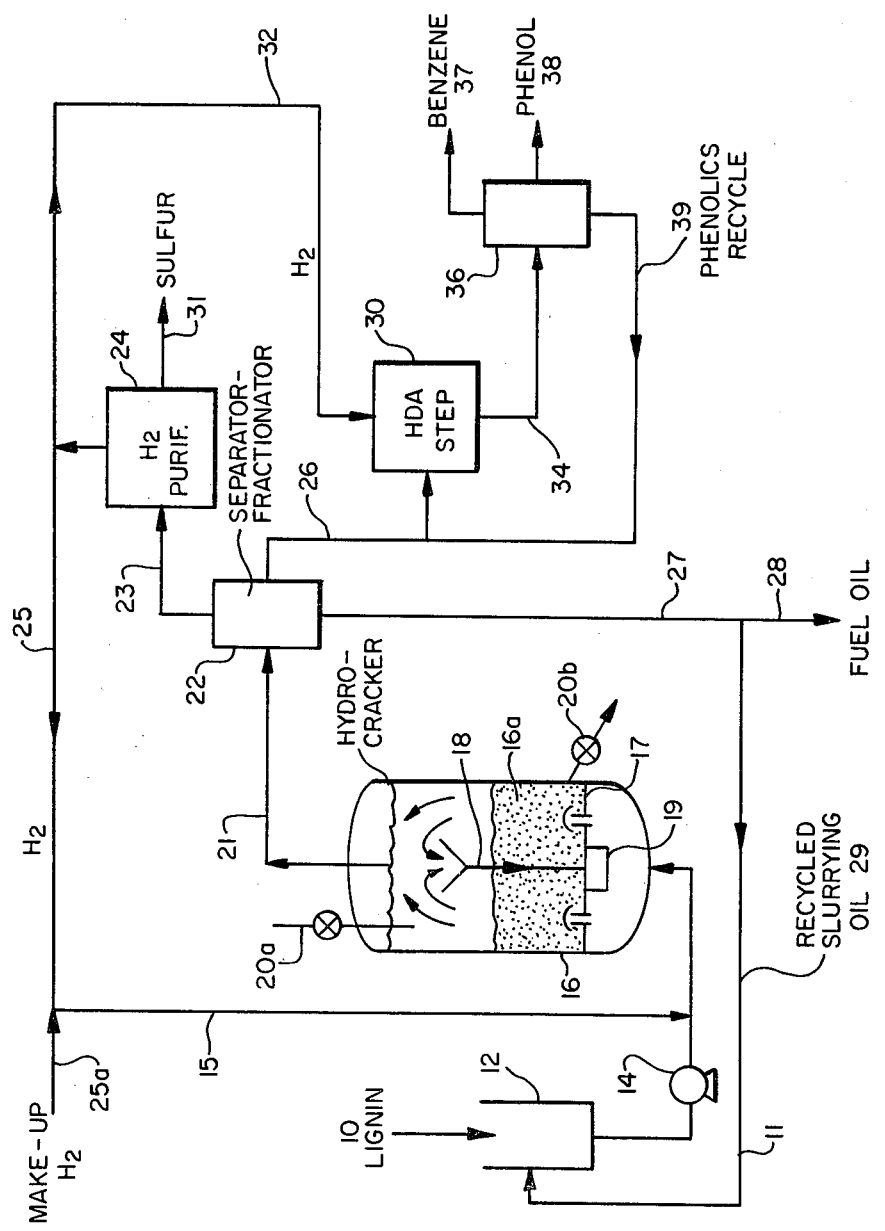
FIG. 3 is a schematic diagram showing the essential process steps of the invention.

As shown in FIG. 3, kraft lignin feed material in particulate form at 10, such as kraft lignin having analysis shown in Table 1, is mixed at 12 with a process-derived oil 11. The resulting slurry feed, containing pulverized lignin and lignin-derived oil, is pressurized at 14 and passed with hydrogen gas at 15 into the bottom of reactor 16 containing catalyst bed 16a. The liquid slurry and gas feed are passed upwardly through flow distributor grid plate 17. The reactor liquid is recirculated through the catalyst bed, passing downward through conduit 18 and recycle pump 19 to grid 17. The liquid feed rate and liquid recycle upward flow velocity maintained in the reactor are sufficient to keep the catalyst bed expanded by 10–150% over its settled height and in an ebullated condition.

The ebullated bed catalytic reactor, which resembles a bed of boiling solids, is ideal for hydrocracking lignin. The random ebullated motion of the catalyst particles promotes good contact and uniform reactor temperatures and helps prevent plugging. The light products formed, such as monoaromatics, vaporize and rise rapidly to the top of the reactor, where they exit as stream 21 before they have time to react further. For effective hydrogenation, the reaction conditions in reactor 16 are usually maintained within the range of 650°–850° F. temperature and 500–2500 psig hydrogen partial pressure. Preferred reaction conditions are 700°–825° F. temperature and 600–2000 psig hydrogen partial pressure. Space velocity used is 0.1–10 weight feed/hr./wt. catalyst, and preferably 0.3–6 weight feed/hr./wt. catalyst. Fresh catalyst is added at connection 20a as needed to maintain desired catalyst activity, and used catalyst is removed at connection 20b.

The effluent 21 from lignin hydrocracking reactor 16 is passed to phase separation-fractionation step 22, from which the gas portion 23 is passed to hydrogen purification unit 24 for removal of sulfur and other impurities at 31. The recovered hydrogen at 25 is recycled to reactor 16 for reuse, while make-up hydrogen is added at 25a as needed. A heavy oil stream having normal boiling range of 500°–900° F. is withdrawn at 27, a portion 28 can be used as aromatic fuel oil, and the remainder is recycled to the slurry mixing tank 12 to provide the required slurrying oil.

The advantage of hydrocracking lignin in an ebullated bed catalytic reactor can be seen by comparing its products yield with that of the Noguchi process, which is a catalytic batch hydrocracking process developed by the Noguchi Institute in Japan. As shown in Table 4, the ebullated bed reactor produced less gas and water, a comparable amount of light distillate, a significantly higher amount of phenols and a lower amount of heavy oils. The phenols distribution of both processes is given in Table 5. If one assumes that the entire phenols yield could be hydrodealylated to produce phenol, the present process would yield 29.9 W % lignin as phenol and the Noguchi process only 17.7 W %.

TABLE 4

LIGNIN HYDROCRACKING PRODUCT DISTRIBUTION (W % of Organic Lignin)

| Process Reactor Type | HRI Continuous Ebullated Bed | Noguchi Batch |
|---|---|---|
| Gas | 25.2 (H$_2$S, CO, CO$_2$, C$_1$-C$_5$) | 17.5 |
| Water | 17.9 | 27.5 |
| Light Distillate | 14.0 (BP < 465° F.) | 14.0 (BP < 464° F.) |
| Phenols | 37.5 (300° F. < BP < 465° F.) | 21.0 (338° F. < BP < 464° F.) |
| Heavy Oil | 11.0 (BP < 465° F.) | 20.0 (BP < 464° F.) |
| Total | 105.7 | 100.0* |

*Noguchi may not have taken hydrogen consumption into account.

TABLE 5

PHENOL YIELDS* FROM LIGNIN HYDROCRACKING COMPARING THE HRI AND NOGUCHI PROCESSES

| | HRI | | Noguchi | |
|---|---|---|---|---|
| Compound | % Phenols produced* | % Phenol calculated** | % Phenol produced* | % Phenol calculated** |
| Phenol | 2.5 | 2.5 | 3.0 | 3.0 |
| Cresol | 9.5 | 8.3 | 10.0 | 8.7 |
| Ethylphenol | 12.5 | 9.6 | 4.3 | 3.3 |
| Propylphenol | 10.5 | 7.5 | 2.0 | 1.4 |
| Xylenol | 2.6 | 2.0 | 1.2 | .9 |
| Unidentified | — | — | .5 | .5 |
| TOTAL | 37.5 | 29.9 | 21.0 | 17.7 |

*Wt %, based on organic content of lignin.
**Based on 100% dealkylation to phenol.

Liquid stream 26 containing the resulting monoaromatics is usually passed to a thermal hydrodealkylation step 30. Hydrogen is added at 32. Dealkylation reaction conditions are maintained within the ranges of 900°–1350° F. temperature and 300–1250 psig hydrogen partial pressure. Following reaction, liquid stream 34 is withdrawn and passed to fractionation unit 36. A phenol product stream is removed at 37 and benzene product at 38. Unreacted alkyl phenols and alkyl benzenes 39 are recycled to hydrodealkylation reactor 30 for further reaction to increase the yields of phenol and benzene.

Based on our present experimental results, it is estimated that lignin can be processed to yield 20.2 W % phenol, 14.4 W % benzene, 13.1 W % fuel oil and 29.1 W % fuel gas. If the hydrogen and fuel requirements of a Lignol process plant are not provided from outside sources, the net fuel oil yield is reduced to 10.9 W %. In this case, hydrogen is generated from the hydrocarbon gas produced in the lignin hydrocracker vent gas stream 23.

The price advantage of phenol over benzene makes it worthwhile to try to obtain higher phenol yields with improved hydrocracking catalysts and with reaction conditions further optimized to improve alkyl phenol selectivities from the present 56% to possibly 80%. If advanced dealkylation techniques could also boost the phenol yield from 60 to 80%, the phenol yield of this Lignol process could be increased from 20 to 38 W %.

Lignin is a renewable resource material which can help reduce use of petroleum feedstocks. The conversion of lignin to phenol and benzene is technically and economically feasible with this Lignol process. Moreover, there is room for further improvement in process economics. A process, such as Lignol, can be used in tandem with the production of fuel ethanol from cellulose. For every gallon of ethanol produced from newsprint, for example, one pound of phenol and 0.7 pound of benzene could be produced. Even more attractive economics could be achieved if the alkyl phenols, such as cresols, ethylphenol, and propylphenols, resulting from lignin hydrocracking were sold as products for specialized applications.

Although we have disclosed certain preferred embodiments of our invention, it is understood that certain adaptations and modifications can be made thereto all within the spirit and scope of the invention, which is defined by the following claims.

We claim:

1. A process for hydrocracking lignin-containing feed materials to produce mono-aromatic phenolic products, comprising:
   (a) mixing the lignin-containing feed with sufficient process-derived slurrying oil to provide a pumpable slurry mixture;
   (b) feeding the lignin and oil slurry with hydrogen into a hydrocracking reaction zone containing an ebullated bed of particulate catalyst;
   (c) maintaining said catalytic reaction zone at temperature within range of 650°–850° F., hydrogen partial pressure of 500–2500 psig, and space velocity within the range of 0.1–10 wt./hr./wt. catalyst;
   (d) phase separating the reaction zone effluent stream to recover a hydrogen-containing gas stream and aromatic oils having normal boiling range of 500°–900° F. as said slurrying oil; and
   (e) withdrawing a mono-aromatic liquid product stream boiling below about 500° F. and containing at least about 25 W % phenolic product.

2. The process of claim 1, wherein the catalyst comprises 12–18 W % molybdenum oxides on alumina support.

3. The process of claim 1, wherein the hydrocracking reaction conditions are maintained within the range of 700°–825° F. temperature and 600–2000 psig hydrogen partial pressure.

4. The process of claim 1, wherein the liquid product from step (e) is passed with hydrogen to a hydrodealkylation step, and the resulting mono-aromatic stream boiling below about 500° F. is fractionated to produce phenol and benzene product while recycling the heavy alkylated phenols and benzenes for further reaction.

5. The process of claim 4, wherein the hydrodealkylation conditions used are temperature within the range of 900°–1350° F. and hydrogen partial pressure within the range of 300–1250 psig.

6. A process for hydrocracking of lignin-containing feed materials to produce mono-aromatic phenolic products, comprising:
   (a) mixing the lignin-containing feed with sufficient process-derived slurrying oil to provide a pumpable slurry mixture;
   (b) feeding the lignin and oil slurry with hydrogen into a hydrocracking reaction zone containing an ebullated bed at a particulate catalyst comprising molybdenum oxides on alumina support;
   (c) maintaining said catalytic reaction zone at temperature within range of 700°–825° F., hydrogen partial pressure of 600–2000 psig, and space velocity within the range of 0.3–6 wt. feed/hr./wt. catalyst;
   (d) phase separating the reaction zone effluent stream to recover a hydrogen-containing gas stream and aromatic oils having normal boiling range of 500°–900° F. as said slurrying oil;
   (e) withdrawing a mono-aromatic liquid product stream boiling below about 500° F. and containing at least about 25 W % phenolics and passing it with hydrogen to a hydrodealkylation step; and
   (f) fractionating the hydrodealkylated stream to product phenol and benzene products.

7. The process of claim 6, wherein the hydrotreating step (e) is performed at conditions of 1000°–1250° F. temperature and 300–1100 psig hydrogen partial pressure.

8. The process of claim 6, wherein a heavy hydrodealkylated material stream from step (f) is recycled to the hydrodealkylation step (e) to increase the yield of phenol and benzene products.

9. The process of claim 6, wherein a portion of the 500°–900° F. aromatic oil is removed as fuel oil product.

* * * * *